United States Patent [19]

Clark et al.

[11] Patent Number: 5,689,070
[45] Date of Patent: Nov. 18, 1997

[54] HIGH TEMPERATURE ELECTROMAGNETIC ACOUSTIC TRANSDUCER (EMAT) PROBE AND COIL ASSEMBLIES

[75] Inventors: Steven P. Clark, Forest; John H. Flora; Daniel T MacLauchlan, both of Lynchburg, all of Va.

[73] Assignee: The Babcock & Wilcox Company, New Orleans, La.

[21] Appl. No.: 506,413

[22] Filed: Jul. 24, 1995

[51] Int. Cl.$^6$ .......................... G01N 29/22; G01N 29/04
[52] U.S. Cl. .......................................................... 73/643
[58] Field of Search .......................... 73/643, 598, 600, 73/622, 629; 367/140; 324/220, 232, 262; 310/208, 254

[56] References Cited

U.S. PATENT DOCUMENTS

| | | | |
|---|---|---|---|
| 4,100,809 | 7/1978 | Bobrov et al. | 73/638 |
| 4,149,421 | 4/1979 | Böttcher et al. | 73/643 |
| 4,184,374 | 1/1980 | Thompson et al. | 73/640 |
| 4,232,557 | 11/1980 | Vasile | 73/629 |
| 4,248,092 | 2/1981 | Vasile et al. | 73/643 |
| 4,296,486 | 10/1981 | Vasile | 367/140 |
| 4,307,616 | 12/1981 | Vasile | 73/643 |
| 4,320,661 | 3/1982 | Peterson et al. | 73/643 |
| 4,578,999 | 4/1986 | Abend et al. | 73/643 |
| 4,593,568 | 6/1986 | Telford et al. | 73/623 |
| 4,594,897 | 6/1986 | Bantz | 73/600 |
| 4,596,147 | 6/1986 | Behl et al. | 73/643 |
| 4,691,572 | 9/1987 | van den Berg et al. | 73/643 |
| 4,777,824 | 10/1988 | Alers et al. | 73/643 |
| 4,976,150 | 12/1990 | Deka | 73/644 |
| 5,140,860 | 8/1992 | Hüschelrath et al. | 73/643 |
| 5,164,921 | 11/1992 | Graff et al. | 367/140 |

OTHER PUBLICATIONS

Maxfield, B.W., A. Kuramoto, and J.K. Hulbert, "Evaluating EMAT Designs for Selected Applications", *Materials Evaluation*, vol. 45, Oct. 1987. Published by the American Scoiety for Nondestructive Testing, Inc., 1987. pp. 1166-1183.

*Primary Examiner*—Hezron E. Williams
*Assistant Examiner*—Rose M. Miller
*Attorney, Agent, or Firm*—Robert J. Edwards; Eric Marich

[57] ABSTRACT

An enhanced EMAT probe and coil construction takes advantage of heat transfer and magnetic flux principles to permit inspection of workpieces at elevated temperatures of 1200° F. and higher. A ferromagnetic, cup-shaped probe assembly having an end cap and a barrel is provided for carrying a coil assembly, preferably one or more permanent magnets, and a frustoconical focus core. The magnets are located within the barrel and connected to the end cap, and the cup-shaped probe assembly positions the coil assembly proximate the surface of the workpiece. A plurality of passageways may be provided in the end cap and barrel for admitting cooling air to an interior portion of the cup-shaped probe assembly. The cup-shaped probe assembly serves to provide a return path for magnetic flux of the magnetic field back to the permanent magnet means. The coil assembly has a coil disk having a matrix of holes and grooves which allow at least one eddy current coil wire to be threaded and interwoven into the coil disk without shorting against itself. A layer of fiberglass cloth covers the coil assembly to thermally and electronically insulate it from the workpiece, providing a durable, rugged and economical construction.

23 Claims, 9 Drawing Sheets

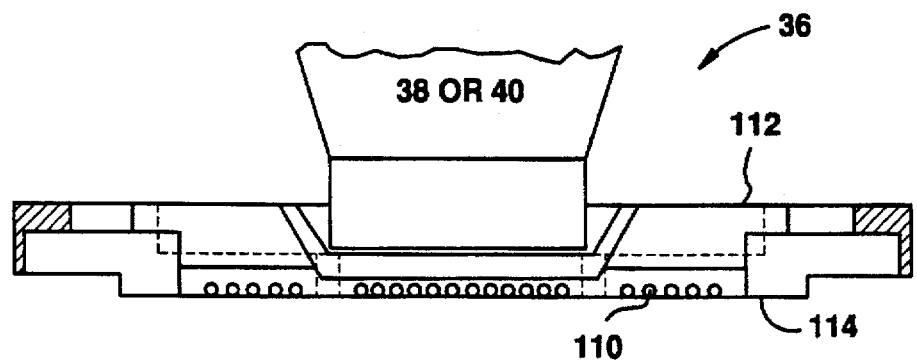
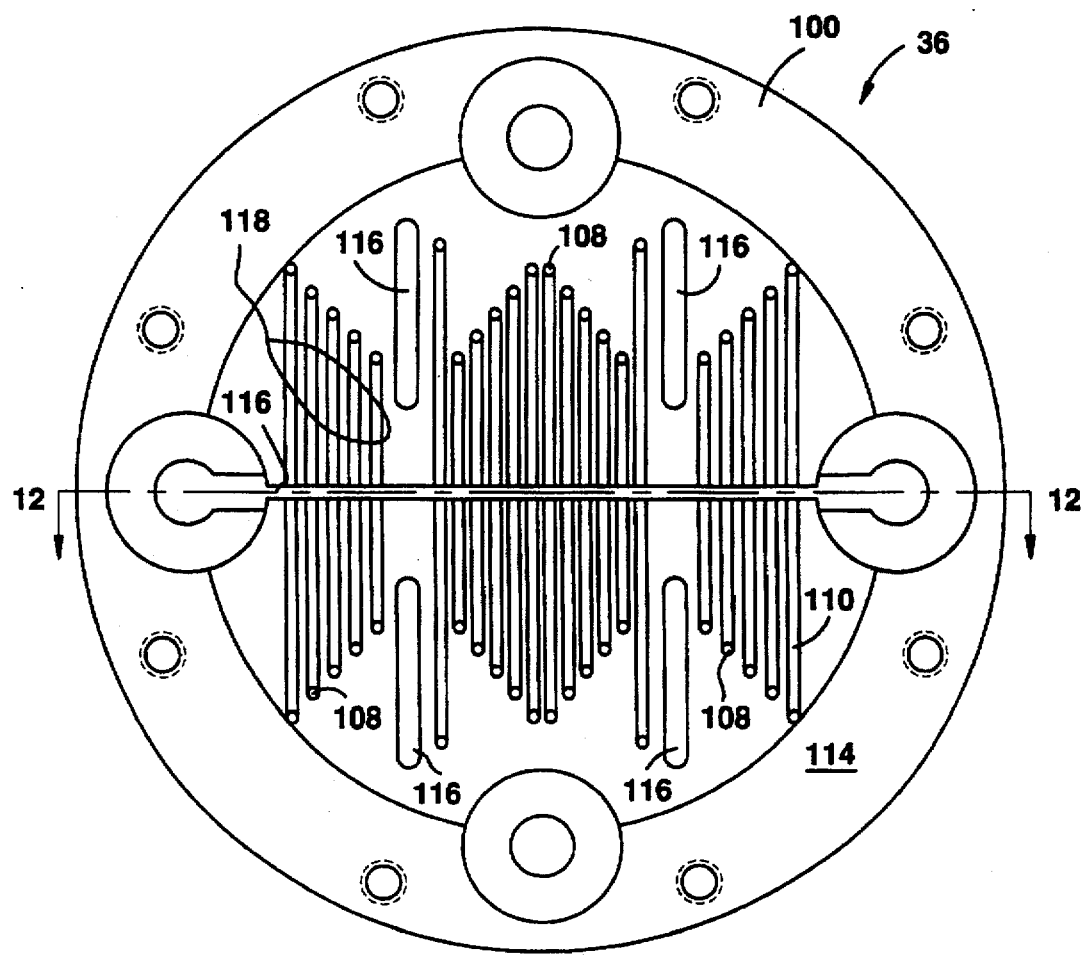

HIGH TEMPERATURE ELECTROMAGNETIC ACOUSTIC TRANSDUCER (EMAT) PROBE AND COIL ASSEMBLIES

FIELD AND BACKGROUND OF THE INVENTION

The present invention relates in general to electromagnetic acoustic transducers (EMATs) and ultrasonic testing and inspection systems utilizing same and, in particular, to enhanced probe and coil constructions which permit inspection of workpieces at elevated temperatures of 1200° F. and higher.

For electrically conductive materials, ultrasonic waves can be produced by electromagnetic acoustic wave induction. Electromagnetic acoustic transducers (EMATs) are the basis of a noncontact ultrasonic inspection method that requires no fluid couplant because the sound is produced by an electromagnetic acoustic interaction within the material. This technique can be used to eliminate the couplant, which complicates testing procedures, slows inspection rates, and can introduce errors into the measurement. In fact, in some cases, conventional ultrasonic tests cannot even be conducted because of the couplant.

In contrast to conventional contact ultrasonic testing, where a mechanical pulse is coupled to the workpiece being inspected in an EMAT, the acoustic wave is produced by the interaction of a magnetic field with induced surface currents. The coil of the EMAT induces eddy currents at the surface of the conductor. A constant magnetic field provided by an AC, DC or pulse driven electromagnet or a permanent magnet is positioned near the coil. The interaction of the magnetic field with the induced eddy currents produces a force called the Lorentz force. This Lorentz force interacts with the material to produce an ultrasonic pulse. As shown in FIG. 1, a simple EMAT 10 consists of a coil of wire 12 and a permanent or electromagnet 14. A strong magnetic field, B, is produced at the surface of an electrically conductive workpiece 16 being tested by the permanent magnet or electromagnet 14. Eddy currents EC with density J are induced in a surface 18 of the workpiece 16 by the coil 12 which is driven at a high excitation frequency by an oscillator (not shown). The Lorentz force F resulting from the alternating current flow in the presence of the magnetic field is transferred to the workpiece 16 and produces an ultrasonic wave UW (with the same frequency as the excitation frequency) that propagates through the workpiece 16.

Various configurations of the coil 12 may be used along with different directions of the magnetic field B to produce a variety of ultrasonic wave modes with unique properties in addition to the conventional longitudinal and shear vertical (S.V.) shear waves. In conductors that are ferromagnetic, a second force (magnetostriction) is added to the Lorentz force, which makes ferromagnetic materials particularly suitable for sensitive EMAT inspection.

The EMAT can be constructed in many configurations. Essential to any EMAT transducer are two components—one or several wire coils to transmit and/or receive a signal, and a magnet to provide a magnetic field. The magnet can be either of the permanent or electromagnet type. The remaining transducer components might include a housing, connectors, fasteners, adhesives, connection wire, coil suspension elements, a wear face, and dielectrics. These components can be fabricated from a variety of materials and into a variety of configurations. The actual materials and configuration for a given transducer depend on the application. Some prior art designs may include transducers which use ceramic (instead of plastic) insulated coil assemblies to increase the working temperature range of the probe.

As indicated above, the EMAT requires a wire coil 12 to function. Typical EMAT coils are wound using insulated wire or are etched from thin copper and Kapton® (a registered trademark of E. I. DuPont de Nemours and Co.) laminate material. The useful temperature range of these constructions is limited to less than 300° F. Coils can also be formed by insulating bare copper wire with electrical insulation made from ceramic compounds. This construction tends to be fragile and susceptible to shattering from dropping or from thermal shock when placed in service in a high temperature application. Useful coil configurations include: spiral, shown in FIGS. 2 and 3, racetrack (a form of spiral) shown in FIG. 4, and meander shown in FIG. 5. In order for the coil configuration to be useful, some EMAT transducers require the coil to be placed between the magnet and the workpiece. Since the effectiveness of the sensor usually increases with magnetic field strength, it is desirable to place the magnet as close to the workpiece as possible. Therefore, a thin coil configuration is usually preferred.

U.S. Pat. No. 4,777,824 to Alers et al. discloses a prior art EMAT construction which includes a generally planar magnetizing coil positioned above the surface of the workpiece, and a generally planar eddy current coil between the magnetizing coil and the workpiece. The coils are preferably packaged in a housing which does not interfere with their operation, but protects them from a variety of adverse environmental conditions. Cooling water can be used to cool the magnetization coil. The disclosed EMAT is said to be operable at temperatures of 2000° F. Utilizing a generally planar magnetizing coil, the patent requires no core for the electromagnet, leading to lower power consumption and cooling requirements.

The process and refining industries use piping and vessels at elevated temperatures up to 1200° F. It is desirable to monitor the integrity of these components while in service, and periodically to monitor any deterioration such as metal loss from corrosion and/or erosion on the inside surfaces. While these conditions can be inspected with conventional piezoelectric ultrasonic transducers in moderate temperature applications below 200° F., at temperatures of 200° F. to 500° F. and higher, conventional ultrasonics become difficult requiring high temperature coupling techniques and special transducers. It is thus evident that another approach is needed to monitor these components. Such an alternative must be compact and portable to facilitate the inspection process of numerous components, and must employ durable, rugged equipment that can withstand the harsh testing environment.

SUMMARY OF THE INVENTION

The present invention permits EMAT inspection of metal vessels and piping for wall thickness, cracks, or other material conditions. Since the EMAT generates the acoustic waves electromagnetically, the need for high temperature gel couplants is eliminated. The specific design of the equipment disclosed herein takes advantage of heat transfer and magnetic flux principles in order to provide a probe and coil which can withstand contact with test components having surface temperatures of up to 1200° F. and higher, while still producing the signals necessary to inspect the part.

Accordingly, one aspect of the present invention is drawn to an electromagnetic acoustic transducer (EMAT) probe assembly for producing an ultrasonic pulse in a workpiece. The probe assembly comprises magnet means for producing a magnetic field in the workpiece and frustoconical focus core means, made of a material having a high magnetic permeability and connected to the magnet means, for focusing the magnetic field at a surface of the workpiece. Coil assembly means are located proximate to an end of the frustoconical focus core means distal from the magnet means, for producing eddy currents at the surface of the workpiece which interact with the focused magnetic field to produce the ultrasonic pulse in the workpiece. Finally, ferromagnetic, cup-shaped probe assembly means having an end cap and a barrel for carrying the coil assembly means, the magnet means and the frustoconical focus core means are provided. The magnet means is located within the barrel and one end is connected to the end cap, and the cup-shaped probe assembly means positions the coil assembly means proximate the surface of the workpiece. The cup-shaped probe assembly serves to provide a return path for magnetic flux of the magnetic field back to the magnet means.

While permanent magnets are preferred because they simplify the EMAT probe assembly construction and cooling considerations in its design, it is understood that the present invention contemplates that suitable magnet means also include A.C., D.C., or pulse driven electromagnets as well as permanent magnets.

Insulation (fiberglass, etc.) or insulated wire would be used to form the cores of such electromagnets as necessary.

Another aspect of the present invention is drawn to a coil assembly suitable for use in an electromagnetic acoustic transducer (EMAT) probe assembly used to produce an ultrasonic pulse in a high temperature workpiece. The coil assembly comprises two main parts, a coil disk and the eddy current coil wire. The coil disk is made of high temperature dielectric material having at least one matrix of holes through the coil disk and grooves on surfaces of both sides of the coil disk which will permit at least one bare, continuous piece of electrically conductive wire to be threaded through and interwoven into the coil disk to produce at least one eddy current coil pattern of a desired configuration on the coil disk while preventing the at least one wire from contacting and shorting against itself. At least one bare, continuous piece of electrically conductive wire is then threaded through and interwoven into the coil disk to produce the at least one eddy current coil pattern of the desired configuration on the coil disk.

Yet still another aspect of the present invention is drawn to an EMAT probe assembly employing the coil assembly described above, to produce an inspection apparatus which is simple in design, rugged in construction, and economical to manufacture.

The various features of novelty which characterize the invention are pointed out with particularity in the claims annexed to and forming a part of this disclosure. For a better understanding of the invention, its operating advantages and specific results attained by its uses, reference is made to the accompanying drawings and descriptive matter in which a preferred embodiment of the invention is illustrated.

BRIEF DESCRIPTION OF THE DRAWINGS

In the drawings:

FIG. 11 is a plan view of the disk of FIG. 9 wherein some of the hidden lines of FIG. 9 have been suppressed for clarity to illustrate just the top face of the disk;

FIG. 12 is a cross-sectional view of the disk of FIG. 11 viewed in the direction of arrows 12—12 of FIG. 11;

DESCRIPTION OF THE PREFERRED EMBODIMENTS

Figure 1:
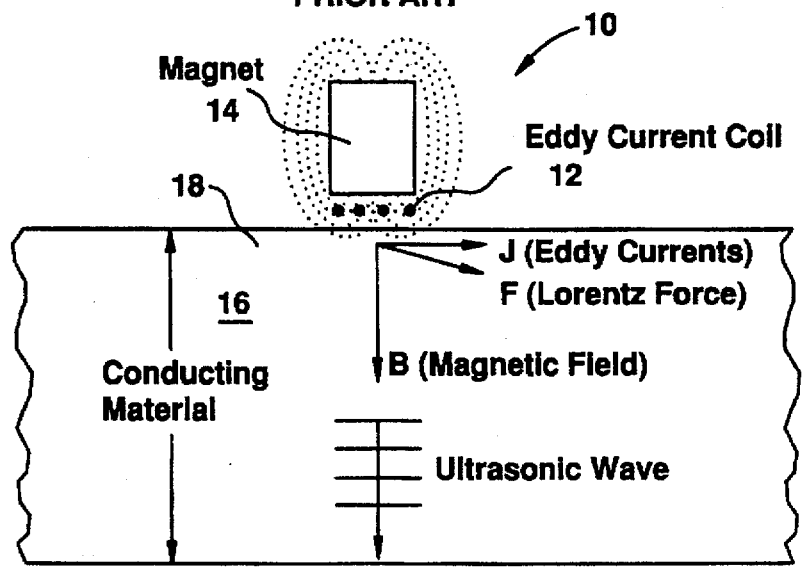
FIG. 1 is a schematic representation of a typical electromagnetic acoustic transducer (EMAT) sensor assembly located adjacent to a workpiece to be tested.
Figure 2:
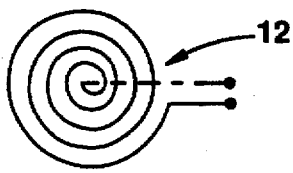
FIGS. 2–3 are schematic representations of known spiral eddy current coil configurations.
Figure 3:
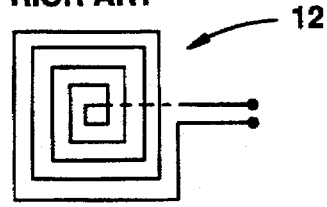
Figure 4:
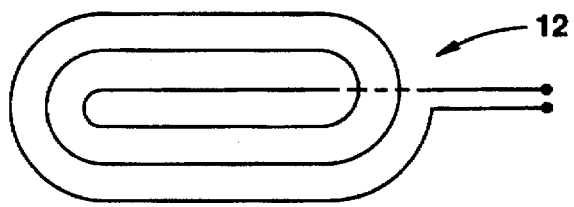
FIG. 4 is a schematic representation of a known racetrack (a form of spiral) eddy current coil configuration.
Figure 5:
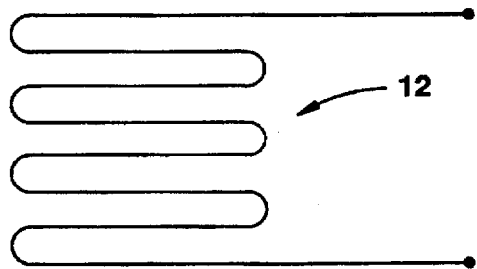
FIG. 5 is a schematic representation of a known meander eddy current coil configuration.
Figure 6:
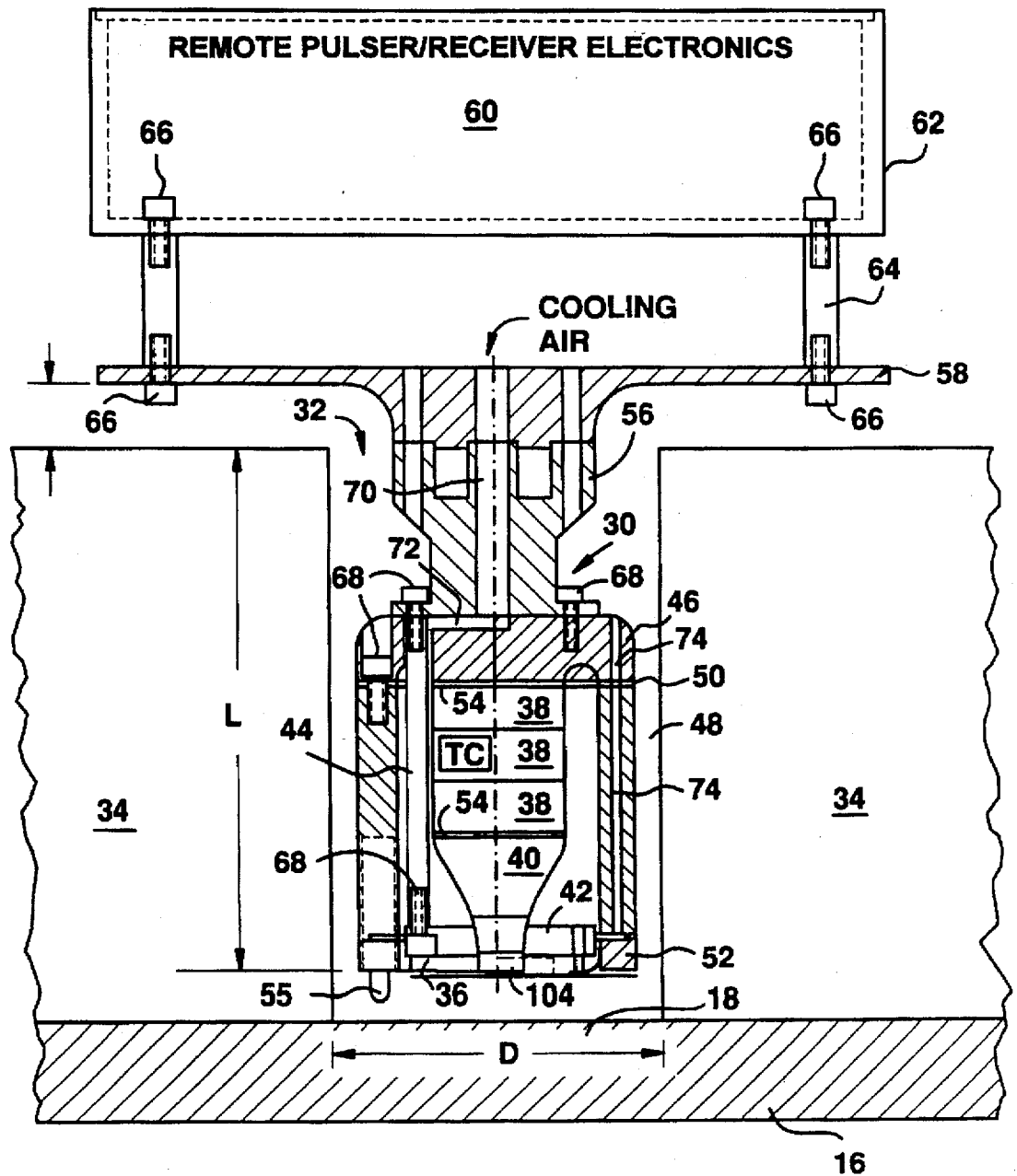
FIG. 6 is a cross-sectional view of an EMAT probe assembly positioned adjacent a workpiece for inspecting same.
Figure 7:
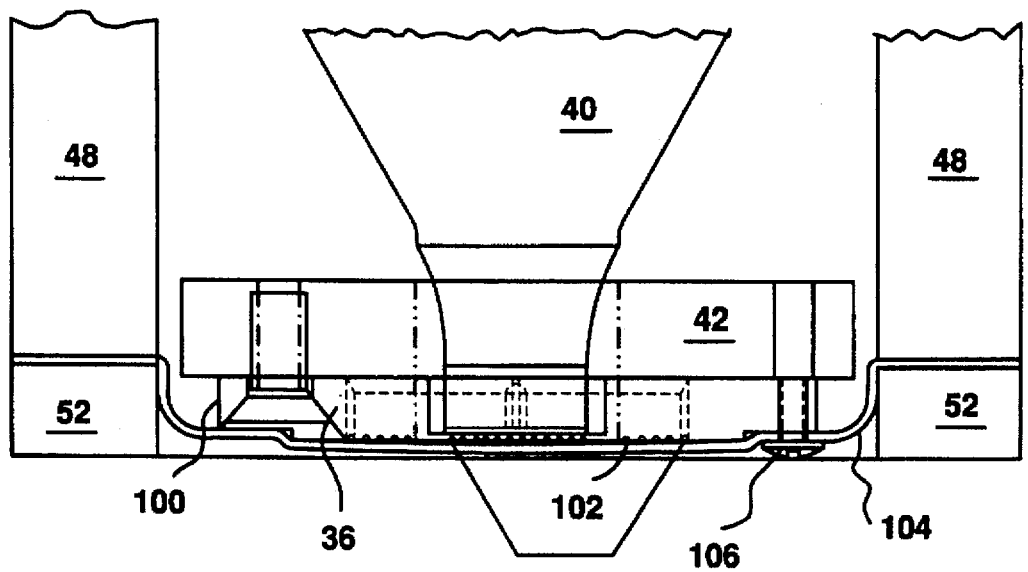
FIG. 7 is a close-up sectional view of the lower portion of the EMAT probe assembly of FIG. 6.

Referring to the drawings generally, wherein like numerals designate the same or functionally similar elements throughout the several drawings, one aspect of the present invention is drawn to an EMAT transducer or probe assembly capable of high temperature (greater than 300° F.) applications. FIG. 6 shows a cross section of the EMAT probe assembly having an inverted, cup-shaped probe assembly 30 according to the invention. The illustrated cup-shaped probe assembly 30, in a preferred embodiment, is designed to fit into a 2.5" diameter (D) by 4.0" deep hole (L) access hole 32 provided through insulation 34 covering the high temperature workpiece 16. However, it can also be used in inspections where access to the workpiece 16 is readily available. The cup-shaped probe assembly 30 includes an eddy current coil assembly 36, one or more (preferably three) permanent magnets 38, and a focus core 40 as shown in FIG. 6. The coil assembly 36 is shown in greater detail in FIGS. 7 and 9–13, described infra, and generally comprises a coil disk 100 and copper wire 102. The copper wire 102 in the coil disk 100 is thermally and electrically insulated from the inspection surface 18 of the workpiece 16 by a layer of fiberglass cloth or other clothlike insulating material 104 which may be attached to and which covers the face of the coil disk 100 by small screws 106. Preferably, and as shown in FIG. 7, the fiberglass layer 104 is clamped inbetween pieces of the cup-shaped probe assembly 30 itself. While FIG. 7 shows both screws 106 and the "clamped" method of attachment, it will be noted that only one method would be required in actual practice.

The coil assembly 36 is attached to an aluminum disk 42 which in turn is fastened to four removably connected aluminum rods 44. While aluminum is mentioned as a preferred material for both the disk 42 and rods 44, the important characteristic in this material choice is having good thermal conductivity. Therefore, copper or other high thermal conductivity materials could also be used. These rods 44 are the primary support for the coil assembly 36 and disk 42. Disk 42 supports and conducts heat away from coil assembly 36. Rods 44 conduct heat away from both of these components.

In the center of the cup-shaped probe assembly 30, behind the coil assembly 36, is a frustoconical shaped focus core 40, preferably made from a material of high magnetic permeability and high saturation magnetization such as Vanadium-Permendur (nominally 50% Co.—nominally 2% V) or Supermendur. These materials are preferably selected to ensure that the frustoconical core means is made of a material which has an intrinsic magnetic saturation of greater than 20 kilogauss when exposed to a magnetization force of 100 Oersteds or less; i.e., a high magnetic permeability and a high saturation magnetization. Materials for the focus core 40 which have a high magnetic permeability but a low saturation magnetization might also be used successfully, but it is doubtful that materials of low magnetic permeability would be useful. The frustoconical shape of this focus core 40 also focuses or concentrates the magnetic flux 41 from the magnets 38 (directly behind the focus core 40) to a location of magnetic interaction 43 as shown conceptually in FIG. 8. The focus core 40 also helps to thermally isolate the one or more magnets 38 from the hot workpiece 16.

The cup-shaped probe assembly 30 comprises four main pieces: an end cap 46, a substantially cylindrical, hollow barrel 48, a shim 50 separating the end cap 46 from the barrel 48, and an end piece 52. The probe assembly 30 is advantageously made of carbon steel. The shim 50, if necessary, only serves to accommodate variations in machining tolerances and, as such, does not form an essential aspect of the invention.

A thin layer of fiberglass cloth 54 is placed between the magnets 38 and focus core 40, and between the one or more magnets 38 and the end cap 46 to provide further insulation. The end cap 46, barrel 48, shim 50, and end piece 52 are all made from ferromagnetic material and function as a return path for the magnetic flux. The end piece 52 can be radiused to adapt the probe assembly 30 for inspection of cylindrical workpieces, such as pipes, having various diameters, thus preventing "rocking" of the probe assembly 30 during contact with the workpiece 16. The barrel 48 may also include several adjustable spring plungers 55 whose purpose is to balance the magnetic attractive force of the one or more permanent magnets 38, thus reducing the force required to remove the probe assembly 30 from the workpiece 16 being inspected. The one or more permanent magnets 38 are preferably made of a magnet material which has an inherently high operating temperature, such as Samarium-Cobalt (SmCo). While other magnet materials such as Neodymium-Iron-Boron (NdFeB) can be produced with higher energy products (MGOe) than SmCo, SmCo was chosen in the preferred embodiment because of its capability of operating at temperatures of 500° F. MGOe's of 22 and higher (28 was used) are preferred.

The end cap 46 is attached to a shaft 56 which is in turn connected to a thermal radiation shield 58 by fasteners (not shown). Remote pulser/receiver electronics 60 are housed in an enclosure 62 which is connected to and separated from the radiation shield 58 by standoffs 64. The cup-shaped probe assembly 30 is held both to the enclosure 62 and together as an assembly by threaded fasteners 66, 68 as well as by the magnetic force provided by the one or more permanent magnets 38. Fasteners (also not shown) would be provided as necessary to hold hollow barrel 48 to end piece 52. When assembled, the nominal weight of the probe, including the remote preamplifier electronics, is less than 4 lbs., which makes it relatively easy to transport and use. The remote electronics 60 in housing 62 allows for long cable lengths between the EMAT probe assembly and other support electronics. The EMAT coil assembly 36 is hard wired into these electronics. Three other connectors (not shown) are also made to the housing 62—signal in, signal out, and power. A handle (also not shown) is also mounted to housing 62 for ease of use.

The cup-shaped probe assembly 30 also uses several passageways to permit forced air cooling of the assembly 30 to extend the temperature range capabilities of the probe and the contact time available for an inspection. These cooling passageways are shown in FIG. 6 and labeled as 70, 72 and 74. Air from fan or compressor means, such as typical plant air at 100 psi (not shown) enters the cup-shaped probe assembly 30 through central passageway 70 which is located along the longitudinal centerline of the shaft 56 and radiation shield 58 and splits preferably into four channels 72 to distribute flow around the four rods 44 which support the coil assembly 36 and then into the interior thereof. The air exits through the layer of porous fiberglass cloth 104 which covers the face of the probe assembly 36 and through the several passageways 74 in the barrel 48 and end cap 46. Air flows out the top of the end cap 46 past the shaft 56 and is deflected across the face of the thermal radiation shield 58. The wires from the coil assembly 36 are brought up through other passageways (not shown) in the end cap 46, shaft 56, and radiation shield 58 for connection to the pulser/receiver electronics 60. Thermocouple means TC may be provided and connected via leads (not shown) to monitor the temperature of the coil disk 100, and/or the one or more permanent magnets 38 to ensure that their temperature does not exceed a maximum operating temperature, and in any event, so that they do not exceed the Curie temperature of the magnets 38. Type K tube and wire style thermocouples will suffice.

As indicated above, another aspect of the present invention is drawn to a coil assembly 36 for a high temperature EMAT probe. As shown in FIGS. 7 and 9-13, the coil assembly 36 is generally comprised of a coil disk 100 machined from high temperature dielectric material (advantageously Vespel® plastic; Vespel® is a registered trademark of E. I. DuPont de Nemours and Co.) and copper wire 102 threaded through and interwoven into the coil disk 100. The thin coil disk 100 (or other shape) of dielectric material is machined with a matrix of holes 108 and grooves 110 in a specific pattern. Grooves 110 are preferably straight, but may be created in an arcuate pattern at defined radii of curvature. The pattern allows a continuous piece of bare copper wire 102 (or other conducting material such as silver, gold, or platinum) to be threaded through the coil disk 100 into a spiral or other eddy current coil form. This process is comparable to stringing a tennis racket except that the wire 102 is threaded in a pattern which prevents the wire 102 from shorting against itself. As the wire 102 is brought through the coil disk 100, it can be crossed over the wire 102 on the opposite side because the coil disk 100 material prevents contact. Modern machine tools allow the construction of coil disks 100 with wire spacings of 0.025" or less when using wire of 0.0159" diameter or smaller. Additionally, by using a milling machine and a small (e.g. 1/64" diameter) ball or other end mill, grooves 110 can be machined in the coil disk 100 to help control the wire position.

Figure 10:
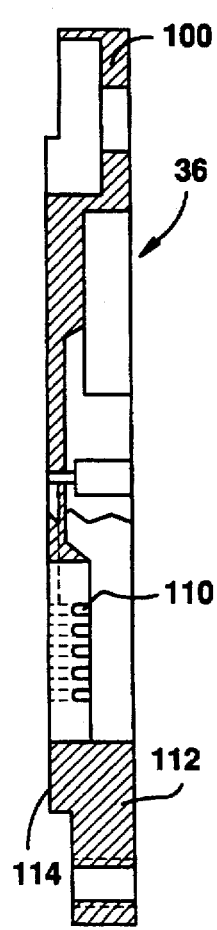
FIG. 10 is a cross-sectional view of the disk of FIG. 9 viewed in the direction of arrows 10—10 of FIG. 9.
Figure 9:
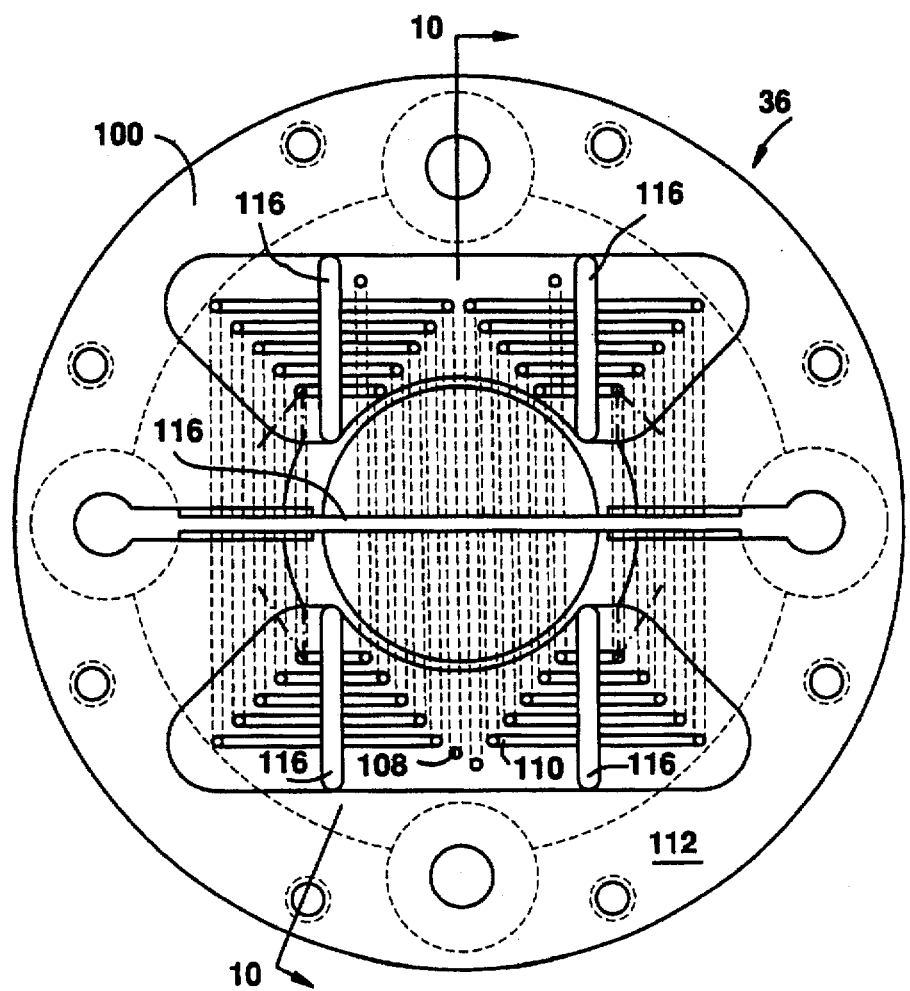
FIG. 9 is a plan view of a disk for an EMAT coil according to the present invention.

FIGS. 9 and 10 show a typical coil disk 100 and a cross-section thereof. FIG. 9 shows the back face 112 of coil disk 100. The drilled holes 108 and machined grooves 110 are shown; hidden lines indicate the grooves 110 on the front face 114. FIG. 11 shows the front face 114 of the coil disk 100 and a close examination of the Figures shows how the machined grooves 110 on the back face 114 relate to the grooves 110 on the back face 112.

Figure 13:
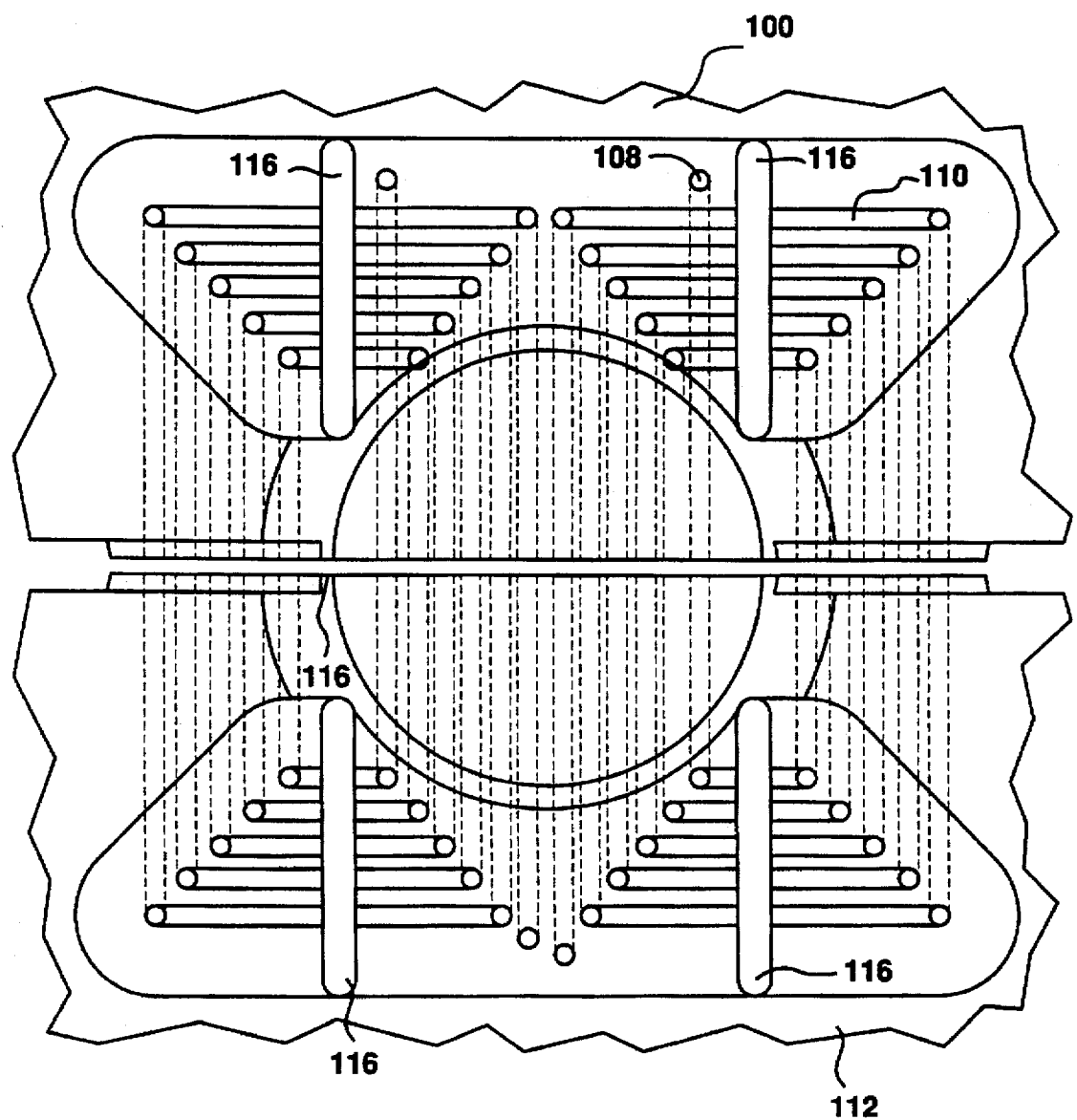
FIG. 13 is a close-up view of a central portion of the disk of FIG. 9 illustrating how the EMAT coil wires are interwoven with the disk.
Figure 13A:
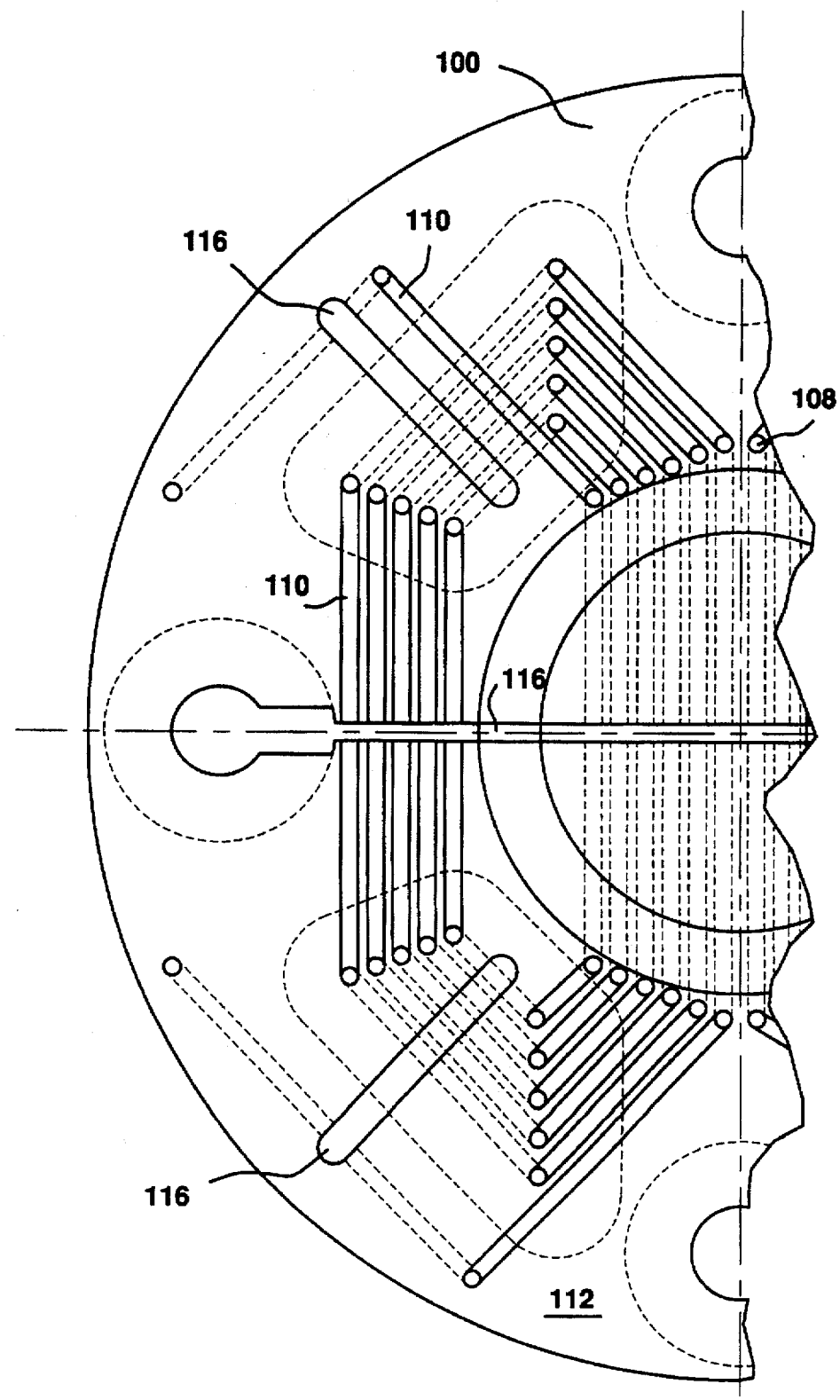
FIG. 13A is a close-up view of a central portion of the disk of FIG. 9A illustrating how the EMAT coil wires are interwoven with the disk.

FIG. 13 shows, from the front face 114, the pattern for threading the wire 102 through the coil disk 100. Note that this coil disk 100 can provide for two (2) spiral eddy current coils. Such a construction is useful if two (2) separate eddy current coil patterns are desired; for example, one being a transmitting coil and the other a receiving coil. The patterns of each coil can be identical or substantially identical to one another or they may be different. The wire 102 is first passed through hole 108 number 1, pulled across the front face 114, returned to the back face 112 through hole number 2, pulled across the back face 112 to hole 108 number 3, and then continued through each hole 108 in numerical order until the wire end is pulled back through hole number 22.

The machining process can be used to manufacture a coil disk 100 suitable for winding a spiral coil, a racetrack coil, a meander coil, or other configurations, including two or more such coils in the same coil disk 100. High temperature plastics and machineable ceramics are typical materials for the coil disk 100. When a plastic is used, such as Vespel®, it usually determines the maximum operating temperature of the coil assembly 36. If ceramic is used, the maximum temperature may be limited by the copper wire 102. Because the coil disk 100 and wire 102 materials will usually have different coefficients of thermal expansion, the coil assembly 36 may also be designed to minimize the strain effects resulting from operating the coil assembly 36 over a large temperature range. These design features include: 1) machining through slots in the coil disk 100, shown as feature 116 in FIGS. 9–13, thereby permitting the coil disk 100 to deflect; and 2) winding the wire 102 with a small amount of slack thereby permitting the coil disk 100 to lengthen more than the wire 102. If the coil disk 100 coefficient of expansion is less than that of the wire 102, then the two described features may not be required. Instead it may be desirable to wind the coil wire 102 tight without slack.

The coil disk 100 must usually fit between a magnet 38 or the focus core 40 and a workpiece 16, and it is desirable to place the magnet 38 as close to the workpiece 16 as possible. This invention facilitates placing the coil wire 102 between the magnet 38 and workpiece 16 while minimizing the magnet 38 to workpiece 16 gap. This is accomplished by the machined grooves 110 in the material in which to lay the wire 102. These grooves 110 can penetrate through most of the disk material, leaving only a few thousandths of an inch of material between the wire 102 and the magnet 38 for electrical insulation. (When the coil assembly 36 is installed in a probe assembly 30, a layer of electrical insulation such as the fiberglass cloth 104 will usually be installed to insulate the wire from the workpiece 16.) Therefore, the thickness of the coil disk 100 between the magnet 38 and the workpiece 16 need only be slightly thicker than the wire 102 diameter or thickness. This construction technique leaves adequate material around the wire 102 to satisfy the structural requirements of the coil disk 100. This is particularly true when a ball end mill is used to machine the grooves 110 since no sharp corners are left at the bottom of the grooves to act as stress risers. Note that coil loops 118 of the eddy current coil run completely across the face of the magnet 38 or focus core 40 and are threaded through the coil disk 100 at locations away from the magnet 38 or focus core 40. Therefore, the coil disk 100 can be significantly thicker at these locations; this facilitates the structural design of the coil disk 100 and permits a wide variety of coil disk 100 and eddy current coil geometry configurations.

Figure 8:
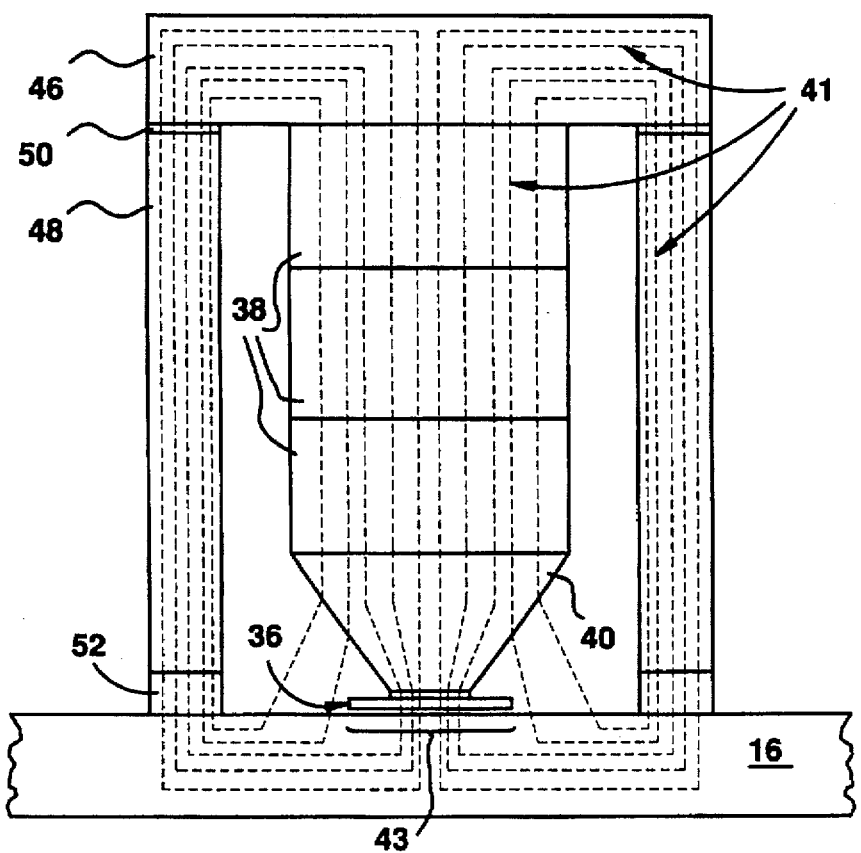
FIG. 8 is a conceptual representation of how the EMAT probe assembly according to the present invention focuses or concentrates the magnetic flux at the surface of a workpiece being inspected to produce an area of electromagnetic interaction.
Figure 9A:
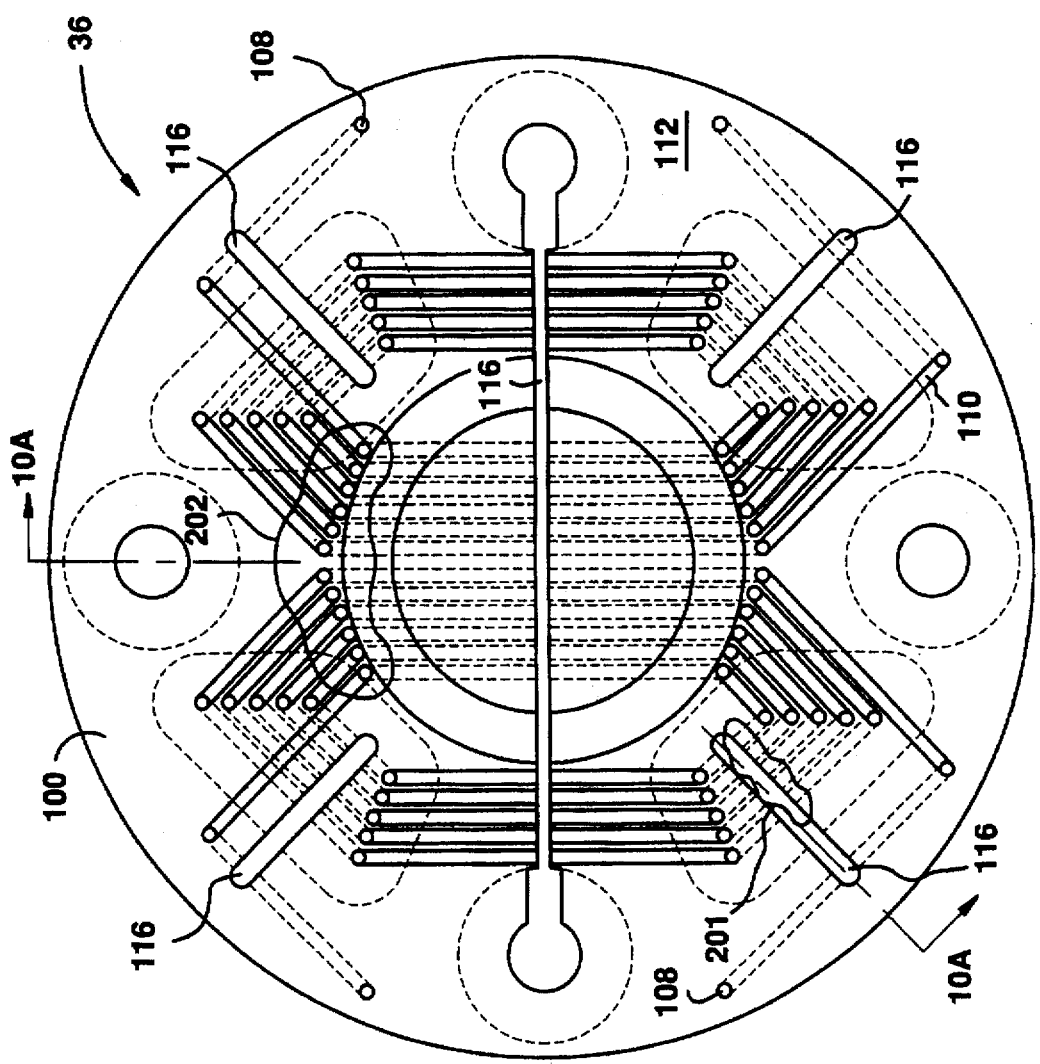
FIG. 9A is a plan view of an alternative preferred embodiment of a disk for an EMAT coil according to the present invention.
Figure 10A:
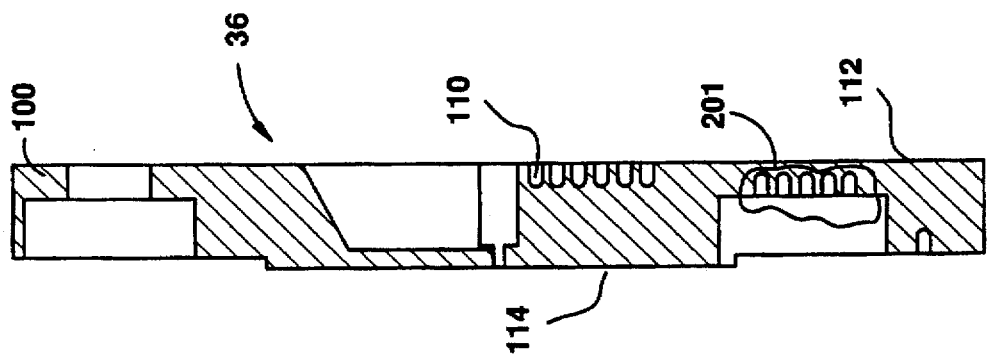
FIG. 10A is a cross-sectional view of the disk of FIG. 9A viewed in the direction of arrows 10A—10A of FIG. 9.
Figure 12A:
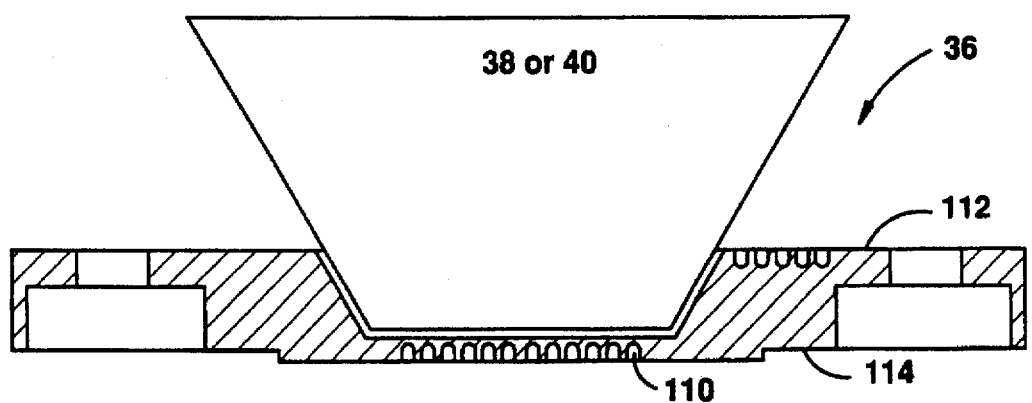
FIG. 12A is a cross-sectional view of the disk of FIG. 11A viewed in the direction of arrows 12A—12A of FIG. 11A.
Figure 11A:
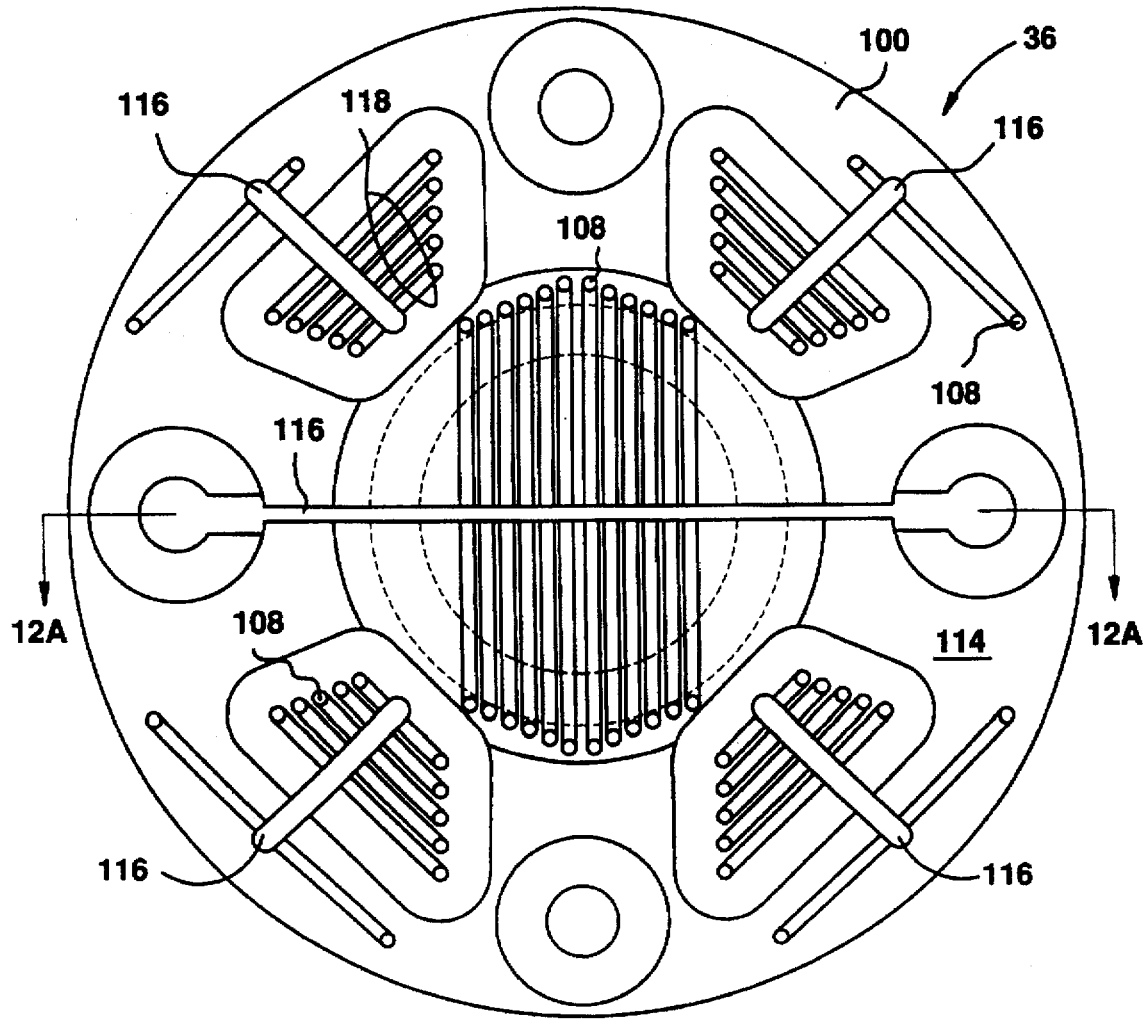
FIG. 11A is a plan view of the disk of FIG. 9A wherein some of the hidden lines of FIG. 9A have been suppressed for clarity to illustrate just the top face of the disk.

During the design and testing of the above-identified embodiment disclosed in FIGS. 6–13, it was determined that a redesign of the coil disk 100 was in order to minimize an undesirable signal which was being generated in the coil assembly 36. The coil disk 100 was redesigned to reduce or eliminate this signal. This signal was the result of parts of the return loop in the coil assembly 36 interacting with the magnetic flux field and the inspected workpiece 16 surface away from the center of the coil disk 100. The basic design change was to minimize the amount of copper wire 102 located in close proximity to the workpiece 16 surface away from the center of the coil disk 100. At the center of the coil disk 100, where the frustoconical focus core 40 concentrates the flux field, the direction of the flux is essentially normal to the workpiece 16 surface. Between this focus core 40 and the coaxial barrel 48 the direction of the flux field becomes tangential to the inspected workpiece 16 surface, as shown in FIG. 8. FIGS. 9A, 10A, 11A, 12A, and 13A show the preferred coil disk 100 geometry. This improved coil disk 100 has actually been produced and its improved performance has been confirmed. As shown in FIGS. 9A and 10A, the improvements are shown as features or areas 201 and 202. Feature 201 shows wire grooves 110 on the front face 114 of coil disk 100 which previously were close to the inspected workpiece 16 surface; now grooves 110 have been recessed away from the workpiece 16 surface. Features 202 shows holes 108 where the wires 102 across the front of the focus core 40 are pulled through the coil disk 100; previously these wires 102 extended further out from the center of the coil disk 100 before going through it. By keeping the through holes 108 closer to the center of the coil disk 100, there is less interaction between these wires 102 and the tangential fields. In any event, it is intended that this revised coil disk 100 geometry be considered as another variation of Applicants' earlier described construction.

Use of the high temperature EMAT probe assembly described above provides the following advantages over the prior art:

The coaxial magnet and core design improves the EMAT technique, improves thermal protection of the magnets, and lends itself to efficient forced fluid cooling if needed to extend temperature range.

The coaxial barrel magnetically couples with the inspection material (when this material is ferromagnetic) to provide a return path for the magnetic flux. The high magnetic permeability core focuses the flux through the EMAT coil. The combination of the barrel and core provide a high density, normal flux field through the inspection material at the location of electromagnetic interaction. With the proper EMAT coil design, this normal flux field is ideal for generating horizontal shear (SH) waves in the material. These SH waves are useful for measuring thickness for example.

The same material that makes the barrel suitable for controlling the flux return, also has a high heat capacity and acts as a radiation barrier between the hot workpiece and the magnets. This helps extend the contact time of the probe for short duration contacts.

The core and the barrel geometries isolate the magnets, by distance, from the heat source.

For longer duration contacts, the coaxial design permits the flow of air through the center of the probe, around the probe components, and out through passageways in the barrel. The fiberglass cloth across the probe face also provides a flow path for the cooling air.

The EMAT coil design is thermally isolated from the inspection piece by the fiberglass cloth. The EMAT coil is mounted to a metal disk of high heat conductance which in turn is attached to similar metal rods which conduct the heat away from the EMAT coils and around the magnets.

The magnets are further isolated thermally by use of thin pieces of insulation.

Spring plungers incorporated in the probe balance the attractive force of the magnets, thereby permitting easy removal of the probe from the workpiece.

The assembly design permits construction of EMAT probes suitable for temporary contact with materials at temperatures greater than 300° F., or continuous contact up to the maximum operating temperature of the magnets. (Such probes are also suitable for temperatures below 300° F.)

For longer contact times, the assembly readily accepts forced air cooling. However, the probe construction permits this without special sealing requirements.

The assembly design permits the construction of a probe which is fastened together solely by mechanical fasteners without the use of adhesives or potting compounds, resulting in a probe which is easier to service and repair.

The design uses shims to permit precise adjustment of the coil to magnet spacing and the coil to workpiece spacing. This provides for a very repeatable transducer from assembly to assembly.

Use of the coil assembly for a high temperature EMAT described above provides the following advantages over the prior art:

The assembly permits construction of EMAT probes suitable for temperatures greater than 300° F. (Such probes are also suitable for temperatures below 300° F. Since the disk coil can be constructed from ceramic or high temperature plastic, and therefore provide the insulation for the copper wires, the operating temperature is limited by the useful operating temperature of the disk or wire, whichever is lower. Insulated wire is not required. This operating temperature will be significantly higher than coils constructed from etched copper/plastic laminate, or wound from insulated wire.

The construction technique results in a coil which is more durable than high temperature coils which are held together using brittle ceramic potting compounds which tend to be fragile.

The grooves and holes in the disk facilitate active, forced fluid cooling which may be used to extend the temperature range of the assembly even further.

The assembly permits the construction of a probe which is fastened together solely by mechanical fasteners without the use of adhesives or potting compounds, resulting in a probe which is easier to service and repair.

While specific embodiments of the invention have been shown and described in detail to illustrate the application of the principles of the invention, those skilled in the art will appreciate that changes may be made in the form of the invention covered by the following claims without departing from such principles. By way of example and not limitation, alternative probe configurations are possible. The probe could include a thin metal wear surface across the front face of the probe. The adjustable spring plungers could be omitted, or spring devices other than spring plungers could be used to balance the attractive force of the magnets. Different core shapes could be used to produce different signal modes for different types of inspections. While permanent magnets are preferred because they simplify the EMAT probe assembly construction and cooling considerations in its design, it is understood that the present invention contemplates that suitable magnet means also include A.C., D.C., or pulse driven electromagnets as well as permanent magnets.

Insulation (fiberglass, etc.) or insulated wire would be used to form the cores of such electromagnets as necessary. The component materials can be varied to change the thermal characteristics of the probe. Since the temperature capability of the probe is largely dependent on the Curie temperature of the permanent magnet, different magnet materials will change the thermal performance of the probe. Finally, the probe could be provided with multiple coil and/or magnet assemblies inside a single barrel assembly.

Changes in the coil assembly are also possible. The coil disk material can be made of any of a number of high temperature dielectric materials including plastics, especially polyimides, machineable ceramics, and grindable ceramics. Besides machining, net shape or near net shape forming methods, such as casting, potting, or injection molding, laminating, and combination methods may also be employed to fabricate the coil disk. The invention can be constructed with or without the recessed machined grooves. Known alternatives for the wire include uninsulated copper wire, insulated copper wire, and other metal conductors in wire or non-wire forms. While the preferred embodiment of the eddy current coil is made by winding and weaving the continuous copper wire through the coil disk, it could also be formed by weaving a plurality of wires through the coil disk and connecting the wires by soldering or other means to complete the eddy current coil.

Thus, in some embodiments of the invention, certain features of the invention may sometimes be used to advantage without a corresponding use of the other features; likewise, some features may be combined to achieve a desired result. Accordingly, all such changes and embodiments properly fall within the scope of the following claims.

We claim:

1. An electromagnetic acoustic transducer (EMAT) probe assembly for producing an ultrasonic pulse in a workpiece, comprising:

magnet means for producing a magnetic field in the workpiece;

frustoconical focus core means, made of a material having a high magnetic permeability and connected to the magnet means, for focusing the magnetic field at a surface of the workpiece;

coil assembly means located proximate to an end of the frustoconical focus core means distal from the magnet means, for producing eddy currents at the surface of the workpiece which interact with the focused magnetic field to produce the ultrasonic pulse in the workpiece;

a metal disk made of high thermal conductivity material attached to the coil assembly means and heat conductive supporting means for supporting and conducting heat away from the metal disk and the coil assembly means; and ferromagnetic, cup-shaped probe assembly means having an end cap and a barrel for carrying the coil assembly means, the magnet means and the frustoconical focus core means, wherein the magnet means is located within the barrel and connected to the end cap, the cup-shaped probe assembly means positions the coil assembly means proximate the surface of the workpiece, and wherein the cup-shaped probe assembly means serves to provide a return path for magnetic flux of the magnetic field back to the magnet means.

2. The EMAT probe assembly of claim 1, wherein the magnet means comprises at least one permanent magnet means made of a magnetic material selected from the group consisting of Samarium-Cobalt (SmCo) and Neodymium-Iron-Boron (NdFeB).

3. The EMAT probe assembly of claim 1, wherein the frustoconical core means is made of a material which has an intrinsic magnetic saturation of greater than 20 kilogauss when exposed to a magnetization force of 100 Oersteds or less.

4. The EMAT probe assembly of claim 3, wherein the frustoconical core means is made of Vanadium-Permendur (nominally 50% CO—nominally 2% V) or Supermendur.

5. The EMAT probe assembly of claim 1, wherein the metal disk to which the coil assembly means is attached is made of a material which comprises one of aluminum and copper.

6. The EMAT probe assembly of claim 1, wherein the metal disk is made of aluminum and the heat conductive supporting means comprises a plurality of aluminum rods removably connected to the aluminum disk and the cup-shaped probe assembly means.

7. The EMAT probe assembly of claim 1, further comprising a layer of fiberglass insulating material which covers a face of the coil assembly means that would be proximate the workpiece when the EMAT probe assembly is used to produce an ultrasonic pulse in the workpiece, the layer of fiberglass insulating material being secured in between the barrel and an end piece connected to the barrel.

8. The EMAT probe assembly of claim 1, further comprising spring-loaded plunger means in the barrel to balance the magnetic attractive force of the magnet means and reduce the force required to remove the EMAT probe assembly from the workpiece.

9. The EMAT probe assembly of claim 1, further comprising an enclosure for housing EMAT pulser/receiver electronics, a thermal radiation shield connected to and interposed between the EMAT probe assembly and the housing to protect the electronics from high temperatures, and a plurality of passageways in the end cap and barrel for admitting cooling air to an interior portion of the cup-shaped probe assembly means and to a top of the end cap where it is deflected across a face of the thermal radiation shield.

10. A coil assembly suitable for use in an electromagnetic acoustic transducer (EMAT) probe assembly used to produce an ultrasonic pulse in a high temperature workpiece, comprising:

a coil disk made of high temperature dielectric material having at least one matrix of holes through the coil disk and grooves on surfaces of both sides of the coil disk which will permit at least one bare, continuous piece of electrically conductive wire to be threaded through and interwoven into the coil disk to produce at least one eddy current coil pattern of a desired configuration on the coil disk while preventing the at least one wire from contacting and shorting against itself; and at least one bare, continuous piece of electrically conductive wire threaded through and interwoven into the coil disk to produce the at least one eddy current coil pattern of the desired configuration on the coil disk.

11. The coil assembly of claim 10, wherein the bare, continuous piece of electrically conductive wire is made of copper.

12. The coil assembly of claim 11, wherein the coil disk is made of a high temperature resistant plastic.

13. The coil assembly of claim 10, wherein the coil disk is made of a high temperature resistant ceramic.

14. The coil assembly of claim 10, wherein the grooves are machined into the surfaces of the coil disk to a depth sufficient to permit the bare wire to lie in the grooves and not extend above the surfaces of the coil disk.

15. The coil assembly of claim 10, wherein temperature induced strain effects resulting from the coil disk and the bare wire have different coefficients of thermal expansion are minimized by machining slots in the coil disk to allow the coil disk to deflect.

16. The coil assembly of claim 10, wherein temperature induced strain effects resulting from the coil disk and the bare wire have different coefficients of thermal expansion are minimized by threading the bare wire through the coil disk with a small amount of slack to permit the disk to expand more than the bare wire.

17. The coil assembly of claim 10, further comprising two separate matrices of holes through the coil disk and grooves on surfaces of both sides of the coil disk, each separate matrix being provided with and permitting at least one bare, continuous piece of electrically conductive wire to be threaded through and interwoven into the separate matrix on the coil disk to produce an eddy current coil pattern of a desired configuration on the coil disk while preventing the at least one wire in each matrix from contacting and shorting against itself; and wherein one of the eddy current coil patterns in one matrix is used as a transmitting coil for producing the ultrasonic pulses in the workpiece and the other eddy current coil pattern in the other matrix is used as a receiving coil for receiving ultrasonic pulses from the workpiece.

18. The coil assembly according to claim 17, wherein the eddy current coil patterns in each of the separate matrices are substantially identical to one another.

19. An electromagnetic acoustic transducer (EMAT) probe assembly for producing an ultrasonic pulse in a workpiece, comprising:

magnet means for producing a magnetic field in the workpiece;

frustoconical focus core means, made of a material having a high magnetic permeability and connected to the magnet means, for focusing the magnetic field at a surface of the workpiece;

coil assembly means located proximate to an end of the frustoconical focus core means distal from the magnet means, for producing eddy currents at the surface of the workpiece which interact with the focused magnetic field to produce the ultrasonic pulse in the workpiece, the coil assembly means having a coil disk made of high temperature dielectric material having at least one matrix of holes through the coil disk and grooves on surfaces of both sides of the coil disk which will permit at least one bare, continuous piece of electrically conductive wire to be threaded through and interwoven into the coil disk to produce at least one eddy current coil pattern of a desired configuration on the coil disk while preventing the at least one wire from contacting and shorting against itself, and at least one bare, continuous piece of electrically conductive wire threaded through and interwoven into the coil disk to produce the at least one eddy current coil pattern of the desired configuration on the coil disk; and ferromagnetic, cup-shaped probe assembly means having an end cap and a barrel for carrying the coil assembly means, the magnet means and the frustoconical focus core means, wherein the magnet means is located within the barrel and connected to the end cap, the cup-shaped probe assembly means positions the coil assembly means proximate the surface of the workpiece, and wherein the cup-shaped probe assembly serves to provide a return path for magnetic flux of the magnetic field back to the magnet means.

20. An electromagnetic acoustic transducer (EMAT) probe assembly for producing an ultrasonic pulse in a workpiece, comprising:

magnet means for producing a magnetic field in the workpiece;

frustoconical focus core means, made of a material having a high magnetic permeability and connected to the magnet means, for focusing the magnetic field at a surface of the workpiece;

coil assembly means located proximate to an end of the frustoconical focus core means distal from the magnet means, for producing eddy currents at the surface of the workpiece which interact with the focused magnetic field to produce the ultrasonic pulse in the workpiece;

an aluminum disk to which the coil assembly means is attached and heat conductive supporting means for supporting and conducting heat away from the aluminum disk and the coil assembly means; and ferromagnetic, cup-shaped probe assembly means having an end cap and a barrel for carrying the coil assembly means, the magnet means and the frustoconical focus core means, wherein the magnet means is located within the barrel and connected to the end cap, the cup-shaped probe assembly means positions the coil assembly means proximate the surface of the workpiece, and wherein the cup-shaped probe assembly means serves to provide a return path for magnetic flux of the magnetic field back to the magnet means.

21. An electromagnetic acoustic transducer (EMAT) probe assembly for producing an ultrasonic pulse in a workpiece, comprising:

magnet means for producing a magnetic field in the workpiece;

frustoconical focus core means, made of a material having a high magnetic permeability and connected to the magnet means, for focusing the magnetic field at a surface of the workpiece;

an aluminum disk to which the coil assembly means is attached and heat conductive supporting means for supporting and conducting heat away from the aluminum disk and the coil assembly means, the heat conductive supporting means including a plurality of aluminum rods removably connected to the aluminum disk and the cup-shaped probe assembly means; and ferromagnetic, cup-shaped probe assembly means having an end cap and a barrel for carrying the coil assembly means, the magnet means and the frustoconical focus core means, wherein the magnet means is located within the barrel and connected to the end cap, the cup-shaped probe assembly means positions the coil assembly means proximate the surface of the workpiece, and wherein the cup-shaped probe assembly means serves to provide a return path for magnetic flux of the magnetic field back to the magnet means.

22. An electromagnetic acoustic transducer (EMAT) probe assembly for producing an ultrasonic pulse in a workpiece, comprising:

magnet means for producing a magnetic field in the workpiece;

frustoconical focus core means, made of a material having a high magnetic permeability and connected to the magnet means, for focusing the magnetic field at a surface of the workpiece;

coil assembly means located proximate to an end of the frustoconical focus core means distal from the magnet means, for producing eddy currents at the surface of the workpiece which interact with the focused magnetic field to produce the ultrasonic pulse in the workpiece;

ferromagnetic, cup-shaped probe assembly means having an end cap and a barrel for carrying the coil assembly means, the magnet means and the frustoconical focus core means, wherein the magnet means is located within the barrel and connected to the end cap, the cup-shaped probe assembly means positions the coil assembly means proximate the surface of the workpiece, and wherein the cup-shaped probe assembly means serves to provide a return path for magnetic flux of the magnetic field back to the magnet means; and a layer of fiberglass insulating material which covers a face of the coil assembly means that would be proximate the workpiece when the EMAT probe assembly is used to produce an ultrasonic pulse in the workpiece, the layer of fiberglass insulating material being secured in between the barrel and an end piece connected to the barrel.

23. An electromagnetic acoustic transducer (EMAT) probe assembly for producing an ultrasonic pulse in a workpiece, comprising:

magnet means for producing a magnetic field in the workpiece;

frustoconical focus core means, made of a material having a high magnetic permeability and connected to the magnet means, for focusing the magnetic field at a surface of the workpiece;

ferromagnetic, cup-shaped probe assembly means having an end cap and a barrel for carrying the coil assembly means, the magnet means and the frustoconical focus core means, wherein the magnet means is located within the barrel and connected to the end cap, the cup-shaped probe assembly means positions the coil assembly means proximate the surface of the workpiece, wherein the cup-shaped probe assembly means serves to provide a return path for magnetic flux of the magnetic field back to the magnet means; and spring-loaded plunger means in the barrel to balance the magnetic attractive force of the magnet means and reduce the force required to remove the EMAT probe assembly from the workpiece.

* * * * *